US010920188B2

(12) United States Patent
Tamargo Martinez

(10) Patent No.: US 10,920,188 B2
(45) Date of Patent: Feb. 16, 2021

(54) CULTURE MEDIUM FOR THE ISOLATION OF CLINICAL SAMPLES OF SPECIES SUCH AS MYCOPLASMA INCLUDING THOSE WHICH ARE NOT CULTURABLE IN TRADITIONAL MEDIA

(71) Applicant: C.P.M. DI CLAUDIO PIERMATTEI E C. S.A.S., Rome (IT)

(72) Inventor: Isis Tamargo Martinez, Madrid (ES)

(73) Assignee: C.P.M. DI CLAUDIO PIERMATTEI E C. S.A.S., Rome (IT)

( * ) Notice: Subject to any disclaimer, the term of this patent is extended or adjusted under 35 U.S.C. 154(b) by 0 days.

(21) Appl. No.: 15/563,368

(22) PCT Filed: Mar. 31, 2016

(86) PCT No.: PCT/IB2016/051824
§ 371 (c)(1),
(2) Date: Sep. 29, 2017

(87) PCT Pub. No.: WO2016/157109
PCT Pub. Date: Oct. 6, 2016

(65) Prior Publication Data

US 2018/0080005 A1 Mar. 22, 2018

(30) Foreign Application Priority Data

Apr. 1, 2015 (IT) ........................ 102015000010601

(51) Int. Cl.
*C12N 1/20* (2006.01)
*C12Q 1/04* (2006.01)
*C12M 1/32* (2006.01)

(52) U.S. Cl.
CPC ............... *C12N 1/20* (2013.01); *C12M 23/12* (2013.01); *C12Q 1/04* (2013.01)

(58) Field of Classification Search
CPC ............. C12N 1/20; C12M 23/12; C12Q 1/04
See application file for complete search history.

(56) References Cited

FOREIGN PATENT DOCUMENTS

| | | | |
|---|---|---|---|
| CN | 102344892 | A | 2/2012 |
| EP | 1600514 | A2 | 11/2005 |

OTHER PUBLICATIONS

"PPLO Media (Mycoplasma Media), PPLO Agar (Mycoplasma Agar Base), PPLO Broth (Mycoplasma Broth Base), Mycoplasma Broth Base (Frey), mycoplasma supplement, Mycoplasma Enrichment w/o penicillin", BD Difco & BBL Manual, 2nd Edition, pp. 1-4.
Atlas, Ronald M., "Handbook of Microbiological Media, fourth edition" Jan. 1, 2010, Taylor and Francis Group, LLC. , pp. 1261-1270 and 1420-1425.
International Search Report and Written Opinion issued in International Application No. PCT/IB2016/051824 dated Jun. 28, 2016.
Smallwood, S, "ATC Medium: 2611 Spiroplasma Medium—Special Modified Formulation", ATCC, XP002751426.
Voros, A et al., "Depleting proteins from the growth medium of Mycoplasma capricolum unmasks bacterium-derived enzymatic activities" Veterinary Microbiology, vol. 138, No. 3-4, Sep. 18, 2009, pp. 384-389.
Brown, D. (2010). Phylum XVI. Tenericutes Murray 1984a, 356vp (Effective publication: Murray 1984b, 33.). In Bergey's Manual of Systematic Bacteriology, 2nd edn, vol. 4, pp. 567-723. Edited by N. R. Krieg, W. Ludwig, W. B. Whitman, B. P. Hedlund, B. J. Paster, J. T. Staley, N. Ward, D. Brown & A. Parte. New York: Springer.

*Primary Examiner* — Ruth A Davis
(74) *Attorney, Agent, or Firm* — Arent Fox LLP

(57) ABSTRACT

The present invention relates to a culture medium specific for microorganisms of *Mycoplasma* genus and, in particular, for species of hardly cultivable *Mycoplasma* (*Mycoplasma genitalium, Mycoplasma pneumoniae, Mycoplasma penetrans, Mycoplasma fermentans, Mycoplasma pirium* and/or *Mycoplasma hyorhinis*). The present invention also provides an in vitro method for the growth and/or isolation and/or identification of species belonging to the *Mycoplasma* genus as well as growth supports using such culture medium.

9 Claims, No Drawings

CULTURE MEDIUM FOR THE ISOLATION OF CLINICAL SAMPLES OF SPECIES SUCH AS MYCOPLASMA INCLUDING THOSE WHICH ARE NOT CULTURABLE IN TRADITIONAL MEDIA

CROSS-REFERENCE TO RELATED APPLICATION

This application is a 35 U.S.C. 371 National Phase of PCT Application No. PCT/162016/051824 filed Mar. 31, 2016, which claims priority to IT Application No. 102015000010601 filed Apr. 1, 2015. The disclosures of these prior applications are hereby incorporated by reference herein.

The present invention relates to a culture medium specific for microorganisms of *Mycoplasma* genus and, in particular, for species of hardly culturable *Mycoplasma* (*Mycoplasma genitalium, Mycoplasma pneumoniae, Mycoplasma penetrans, Mycoplasma fermentans, Mycoplasma pirium* and/or *Mycoplasma hyorhinis*). The present invention also provides an in vitro method for the growth and/or isolation and/or identification of species belonging to the *Mycoplasma* genus as well as growth supports using such culture medium.

STATE OF PRIOR ART

Mycoplasmas are the smallest microorganisms capable of living freely, they differentiate from viruses for their capability of growing in media without cells, by multiplying by binary fission and they distinguish from bacteria for the lack of cell wall; however, they are provided with a cell membrane, formed by three layers including sterols, substances which can be found neither in bacteria nor viruses, providing support to the structure (1-9).

They are capable of surviving without cell wall if they keep in an osmotically stable culture medium including the whole protein complex necessary for the multiplication thereof. This type of conditions can be found in an animal organism or in cell culture media or in culture media with highly complex formulations.

The bacteria of *Mycoplasma* genus (Mycoplasmataceae family, Mycoplasmatales order) belong to the Mollicutes ("smooth skin") class and they represent a group of complex and sophisticated microorganisms, unique for the nature thereof among prokaryotes, which currently are an enigma for microbiologists.

They are mostly widespread in nature and, currently, the number of known species is increasing and it is about 200, many of them behave as commensal, whereas other species are pathogenic both for man and animals and plants (7-14)

In the human being, 14 species were isolated, 12 thereof belong to the *Mycoplasma* genus and 2 specie (*Ureaplasma* biovar *parvum* and *Ureaplasma urealyticum*) belong to the *Ureaplasma* genus. Six out of 14 species are mainly localized in the urogenital tract (14-21)

The *mycoplasma* have 3 main biological features which make them unique with respect to the remaining bacteria and which characterize the behaviour thereof in relation to the host organism. Such features are:

1—absence of cell wall and smallest size known in a microorganism living freely, both as to the cell size thereof (0.2-0.8 μm) and as to the genoma size. In this way, *Mycoplasma genitalium* has the smallest genoma (580 kb and only 381 genes) included in a cell capable of autoreplicating and the genic content thereof determines the minimum number of genes essential for the DNA replication and repair, and for the genetic transcription and translation;

2—limited provision of metabolic routes. The complete characterization of genomes of *Mycoplasma pneumoniae* and *Mycoplasma genitalium* demonstrated the absence of genes involved in the synthesis of amino acids and the poor presence of genes for the biosynthesis of vitamins, precursors of nucleic acids, fatty acids and cholesterol, therefore they wholly depend upon their own exogenous supply, coming from the cells of the host organism or from the complex and enriched culture media, which notwithstanding the complex composition thereof allow the growth only of the most demanding *Mycoplasma* species, in a period of two weeks or more;

3—microorganism-host interaction, which appear as surface parasitism with the cells of epithelium and the cells of the immune system and as intracellular localization of facultative form (capability of preserving both in vitro extracellular and intracellular vitality), of some species.

The genome size and the composition of the bases thereof constitute the main properties of the *mycoplasma*. Proportionally to their own sizes, the *mycoplasma* species have genomes ranging from 600 to 2300 kb. *Mycoplasma pneumoniae*, for example, has a genome of 816 kb, whereas that of *Mycoplasma genitalium* is even smaller, as it is 580 kb and currently, in the most advanced studies, one tends to take as reference for the research the smallest genomic set, required with the purpose of allowing an autonomous vitality.

Therefore one can understand that for the replication of these agents complex nutritional requirements are imposed, as they are lacking in several enzymatic routes characterizing most part of bacteria and they exclusively depend upon outer sources of biosynthetic precursor such as amino acids, nucleotides, fatty acids and sterols (22-26).

The identification of the different *Mycoplasma* species and the laboratory diagnosis are based upon fundamental bacteriological tests, such as: morphology, strains' features, biochemical and physiological tests. The implementation of these tests requires the culture of the strains, which for some species results to be difficult, complex and expensive.

The growth of the mycoplasmas of human origin has to be implemented only by isolating species with a defined pathogenic potential and a reasonably satisfying growth in specific and standardized culture media, such as *Ureaplasma* spp., *Mycoplasma hominis* and *Mycoplasma pneumoniae*. All *mycoplasma* species require complex culture media, constituted by sterols, fatty acids, amino acids and other compounds satisfying the nutritional requirements. The processing thereof is very careful and it requests checks of all and every component thereof. For this reason, few clinical laboratories offer the culture as diagnostic method of infections from *mycoplasma*. However, the culture remains fundamental for the biological and molecular characterization of the clinical isolates, including the resistance studies.

The extremely irritating species such as *Mycoplasma genitalium, Mycoplasma fermentans, Mycoplasma penetrans* and *Mycoplasma pirum* have to be detected with molecular techniques (27-30)

After developing the molecular techniques for the microbiological diagnosis, currently methods for analysing genomic DNA, ribosomal RNA and others have been developed, notwithstanding they are expensive methods and some of these methods can be applied only in laboratories provided with sophisticated equipment, with highly qualified personnel. However, currently there are molecular techniques adequately valid for the diagnostics only for some species of mycoplasmas, whereas others have been studies due to the development complexity and high costs.

Summarizing, the known existing culture media are used mainly as instrument for proliferating and growing *Mycoplasma* strains.

Variations in the composition of known media allowed to identify some species of mycoplasmas characterized by relatively fast growth, such as in case of culture media including amino acids such as arginine for the culture of *Mycoplasma hominis* or urea for species such as *Ureaplasma parvum* and *Ureaplasma urealyticum*. In case of *Mycoplasma pneumoniae* it can be cultured by using culture media on the market including glucose, but the growth can be obtained only after several weeks.

In case of the most demanding species, such as for example, *Mycoplasma genitalium* the identification currently takes place by means of molecular techniques, available on the market. However, these methods do not allow to identify species with clinical importance such as *Mycoplasma fermentans, Mycoplasma penetrans, Mycoplasma pirum*. In the current praxis in order to isolate such strains starting from samples one proceeds by inoculating the same in cell cultures. However, the obtaining of colonies requires very long time even in the order of several months.

The culture and identification of particular species of *Mycoplasma* such as, for example, *Mycoplasma genitalium, Mycoplasma pneumoniae, Mycoplasma penetrans, Mycoplasma fermentans, Mycoplasma pirium, Mycoplasma hyorhinis* has a series of disadvantages, in primis that of requiring very long incubations for several days, if not weeks (31). For this reason, for some species of *Mycoplasma* the molecular methods remain the first choice. However, the conventional cultures are unavoidable for the microbiological characterization of microorganisms.

Different epidemiological, genetic and molecular studies suggest that the infective processes from agents such as *Mycoplasma genitalium* and *Mycoplasma hominis* can contribute to the development of certain malign processes, including prostate and uterine cancer up to 20% of cases. *Mycoplasma genitalium, Mycoplasma penetrans* and *Mycoplasma hyorhinis* are sexual transmission agents and it was observed that they are capable of transforming the normal epithelial cells into malign ones after an infective process.

These species are further related, with relative frequency, to non-gonococcal urethritis and they can be found in 15-20% of asymptomatic men, with different chronic process and infertility.

The need for developing a culture medium even allowing isolation and identification of species di *Mycoplasma* difficult to be cultivated then remains an open problem in the state of prior art.

The object of the present invention is then to propose a new and original solution to the problems existing in the state of known art and related to isolation and identification of species of *Mycoplasma* genus.

SUMMARY OF THE INVENTION

The present invention derives from the need for developing a culture medium allowing effectively and quickly to cultivate, isolate and identify at the same time different species belonging to the *Mycoplasma* genus and, in particular, the species hardly to be cultivated, such as for example, *Mycoplasma genitalium, Mycoplasma pneumoniae, Mycoplasma penetrans, Mycoplasma fermentans, Mycoplasma pirium* and/or *Mycoplasma hyorhinis*.

For the first time then a culture medium is described allowing the growth of most species of *Mycoplasma* genus and which then makes possible to extend the microbiological culture techniques to a wide spectrum of species of *Mycoplasma* genus.

In particular, the inventors after long experimentation and selection work detected the main ingredients for the formulation of a culture medium allowing to satisfy the abovementioned needs. In particular, the composition of the culture medium of the invention comprising main ingredients with different origins and compositions, unexpectedly revealed to be capable of allowing the abundant growth of the species of *Mycoplasma* genus. The presence of the hydrolysate of animal blood and tissue in the culture medium of the invention results to be particularly important, which guarantees the supply of substances necessary for the growth of *Mycoplasma* spp, without impeding identification.

One of the advantages associated to the invention consists in the fact that the identification of the interesting bacteria can be performed based upon the culture features only (colour of the medium), allowing to exclude the need for observing deeply the morphological features of the colonies, by easing the interpretation of the results by a not specialized personnel.

The culture medium of the invention, comprising nutritional substances sufficient for the quick growth of the interesting microorganisms and hampering the growth of other concurrent organisms, allows a quicker development of the *mycoplasma* which, then, can be isolated and identified in much shorter time than the cultures utilizing known culture media. In particular, isolation and identification can take place even after a maximum period of incubation of 1-4 days.

An additional advantage of the culture medium of the invention lies in the fact that it does not comprise toxic substances or environmental contaminants which can limit the production and use thereof.

The subject of the present invention are:

- a culture medium for microorganisms of *Mycoplasma* genus comprising as active ingredients:
  - hydrolysate of bovine blood,
  - extract from beef heart;
  - enzymatic hydrolysate of bovine heart;
  - enzymatic hydrolysate of milk proteins;
  - enzymatic hydrolysate of soybean proteins;
  - enzymatic hydrolysate of animal tissue;
  - autolysate or hydrolysate from *Saccharomyces cerevisiae;*
- a method for in vitro cultivation and/or isolation and/or identification of microorganisms of *Mycoplasma* genus comprising a step of culturing microorganisms by using the culture medium of the invention;
- a support for the growth and/or isolation and/or identification of microorganisms belonging to the *Mycoplasma* genus comprising a culture medium of the invention;
- a kit for the growth and/or isolation and/or identification of microorganisms belonging to the *Mycoplasma* genus comprising at least an aliquot of the culture medium of the invention and means suitable to allow the growth and/or isolation and/or identification of said microorganisms.

Other advantages and features of the present invention will result evident from the following detailed description.

DESCRIPTION OF THE INVENTION

A detailed description of the different subjects of the present invention is reported hereinafter.

Culture Medium

The present invention provides to a culture medium for microorganisms of *Mycoplasma* genus. In particular, the culture medium of the invention can be used for the species of *Mycoplasma* selected from the group comprising: *Mycoplasma genitalium, Mycoplasma pneumoniae, Mycoplasma penetrans, Mycoplasma fermentans, Mycoplasma pirium, Mycoplasma hyorhinis, Mycoplasma hominis* and other species of *Mycoplasma* spp., existing in the usual flora of the human being and of the animals. It can even be used for microorganisms such as *Ureaplasma urealyticum* and *Ureaplasma* spp.

The culture medium of the invention comprises as active ingredients hydrolysate of bovine blood, extract from beef heart; enzymatic hydrolysate of bovine heart; enzymatic hydrolysate of milk proteins; enzymatic hydrolysate of soybean proteins; enzymatic hydrolysate of animal tissue; autolysate or hydrolysate from *Saccharomyces cerevisiae.*

All ingredients mentioned herein, both they are main ingredients and the further ingredients/components of the culture medium of the invention, are available on the market and therefore they do not need herein particular further examinations. However, by way of example, for some of them a brief further examination is given here below.

The hydrolysate of bovine blood is the end product obtained from the separation and dehydration of the bovine blood with protein properties which reach values higher than 80% by making it a unique source of proteins. 45% of the blood volume are cells, red cells (most part), white cells and blood platelets. The remaining blood is constituted by plasma, a clear and yellowish liquid. The plasma, which is constituted by 45% by water, even includes nutrients such as glucose, fats, proteins, vitamins, minerals and amino acids necessary for the protein synthesis. By way of example, the hydrolysate of bovine blood can be prepared by diluting the blood 1:2 in NaCl 0.5% and by heating the mixture at about 80° C. for about half an hour. Subsequently, one proceeds with centrifugation and sterilization, preferably, by means of filtration.

The hydrolysate of bovine blood can be present in an amount between about 5 and 30 grams per litre of culture medium.

The enzymatic hydrolysate of animal tissue is a set, both amino acids and the peptides with low molecular weight and all metabolites owned by a cell.

In particular, such ingredient is obtained from the enzymatic protein hydrolysis of the animal tissues, under particular physical-chemical conditions of pH and temperature. From the chemical point of view, what is obtained is the degradation of the proteins included in the outer cellular membrane, in the nuclear membrane and in the cytoplasmic matrix, by releasing the cellular content formed by metabolites owned by the cell, including the nucleus content. Such hydrolysate is also known as peptone with animal origin. By way of example and not with limitative purpose, to the purposes of the present invention Proteose Peptone can be used, produced by OXOID, Beef Extract, Bacto™.

The quantity of enzymatic hydrolysate of animal tissue can be comprised between about 2 and 99 grams per litre of culture medium.

The enzymatic hydrolysate of milk proteins, which can be casein hydrolysate, derives from the casein hydrolysis with hydrochloric acid, followed by the neutralization with sodium bicarbonate. The casein hydrolysed acid provides the nitrogen necessary for the culture medium. By way of example and not with limitative purpose, the casein hydrolysate usable for the purpose of the present invention is the one produced by OXOID.

The enzymatic hydrolysate of milk proteins, which can even be lactalbumin hydrolysate, is a peptone deriving from the pancreatic digest of the protein lactalbumin obtained from milk. The high levels of main amino acids make it a precious supplement in the culture media of tissues. By way of example and not for limitative purpose, the hydrolysate usable for the purposes of the present invention is the one produced by BD Bacto™ (Lactalbumin Hydrolysate, Enzymatic digest of lactalbumin Code:259962—BD Bacto™ Leche Peptonizada BD).

The enzymatic hydrolysate of milk proteins can be present in an amount between about 1 and 67 grams per litre of culture medium.

As far as the enzymatic hydrolysate of soybean proteins is concerned, by way of example and not for limitative purpose the PEPTONE DI SOIA BBL™ is reported.

The enzymatic hydrolysate of soybean proteins can be present in an amount between about 0.2 and 34 grams per litre of culture medium.

Relatively to the autolysate or hydrolysate from *Saccharomyces cerevisiae* it can be prepared, for example, by dissolving 100 gr of *Saccharomyces cerevisiae*, previously cultured and centrifuged, in 100 mL of distilled water. Subsequently it is autoclaved for 10 minutes at 121 degrees, it is sterilized by means of filtration.

The autolysate or hydrolysate from *Saccharomyces cerevisiae* can be present in an amount between about 15 and 56 grams per litre of culture medium.

In particular, the extract from beef heart can be present in the culture medium in an amount between about 2 and 56 grams per litre of culture medium. Preferably such ingredient is present in an amount comprised between about 10-20 grams per litre of culture medium.

It comprises specifically prepared peptones, comprising meat digest (which can be processed starting from heart, brain, etc) prepared by means of enzymatic digestion of selected fresh meats, aimed at improving the development of very demanding microorganisms. It includes a high spectrum of peptides with different volumes available in each peptone, with minerals, vitamins, nucleotides and other carbonate compounds existing in the single peptones.

In the production of Peptones only the hydrolases are used, and more in particular those operating peptide bonds of proteins (protease) and peptides (peptidase) with animal, vegetable and microbial origin. The uses of these enzymes vary upon the direct addition of tissue or other organs, such as pancreas, aimed at using highly purified enzymes. An example of enzymes used in the hydrolysis of proteins is constituted by papain. Papain has a wide action spectrum (proteinase with wide spectrum) as practically it digests all bodies with protein origin, even keratin, polypeptides and synthetic substrates aimed at amino acids.

The protein hydrolysis can be performed by using two types of hydrolysing agents, chemical (acid or alkaline) agents or enzymes.

The acid hydrolysis is used to obtain a small number of nutrient bases, typically by using substrates such as meat, heart, etc.

As hydrolysing agents mineral acids are used such as hydrochloric acid, sulphuric acid, etc. The hydrolysis is obtained at temperature from 100 to 130° C. and pressure of 1-4 atmospheres in a time ranging from 4 to 45 hours. These pressure and temperature conditions considerably increase the hydrolysis degree and consequently a high content of free amino acids is obtained.

Alkaline hydrolysis. The alkaline hydrolysis is performed by using, as hydrolysing agents, sodium, calcium and ammonium hydroxides.

The enzymatic hydrolysis allows recovering considerable amounts of amino acids, peptide and polypeptides of the original material. The "soft" condition, wherein the enzymatic hydrolysis takes place, allows eliminating or mitigating some of the disadvantages which the acid and alkaline hydrolyses have and the obtained products reach a high level of assimilation by microorganisms. Several enzymatic preparations (pancreatin, hepatopancreatin, etc.) are used.

The quantity of enzymatic hydrolysate of bovine heart can be comprised between about 1 and 62 grams per litre of culture medium.

The presence of the above-mentioned components makes that the culture medium has a high total nitrogen content. In particular, such content is comprised between about 10% and 94%.

In an embodiment of the invention, the culture medium further comprises even growth inhibitors of Gram-negative microorganisms, Gram-positive, fungi and yeasts. In particular, such inhibitors can be selected from the group comprising nalidixic acid, vancomycin, nystatin, thallium acetate, phenol red, penicillin and amphotericin B.

Preferably, inside the culture medium the nalidixic acid is present in an amount comprised between 0.1 and 3.5 grams per litre of culture medium; and/or vancomycin is present in an amount comprised between 0.5 and 1 gram per litre of culture medium; and/or nystatin is present in an amount comprised between 0.2 and 5 grams per litre of culture medium; and/or the thallium acetate is present in an amount comprised between 0.01 and 1.5 grams per litre of culture medium; and/or the phenol red is present in an amount comprised between 0.03 and 3 grams per litre of culture medium; and/or penicillin is present in an amount comprised between 0.1 and 5 grams per litre of culture medium; and/or amphotericin B is present in an amount comprised between 0.05 and 3 grams per litre of culture medium.

In particular in presence of phenol red the following colour changes are noted for the below mentioned species:

*Mycoplasma hominis*: Red/Turbid Red
*Ureaplasma urealyticum*: Red
*Ureaplasma parvum*: Red
*Mycoplasma pneumoniae*: Turbid Yellow
*Mycoplasma genitalium*: Orange-coloured/Yellow
*Mycoplasma fermentans*: Brilliant Yellow/Turbid Yellow
*Mycoplasma pirum*: Yellow/Turbid Yellow
*Mycoplasma penetrans*: Brilliant Yellow/Turbid Yellow
*Mycoplasma hyorhinis*: Turbid Yellow The culture medium can further comprise even salts of trivalent metals, preferably ferric ammonium citrate; aromatic amino acids; mixture of globular proteins and plasma.

The plasmatic or globular protein usable in the culture medium, for example, can be obtained from horse, rabbit and bovine blood. By way of example, the process can provide centrifugation of the total blood, freezing of the obtained supernatant −80 degrees for 48 hours, freezing and dilution 1:8 with saline solution. It is additioned to the prepared culture and the obtained medium is frozen at −20 degrees until the use thereof.

Preferably the salts of trivalent metals are present in an amount comprised between about 0.5 and 1.0 grams per litre of culture medium; the aromatic amino acids are present in an amount comprised between about 1 and 72 grams per litre of culture medium; the globular and plasmatic proteins are present in an amount comprised between about 0.01 and 70 grams per litre of culture medium; the mixtures of fibrous proteins are present in an amount comprised between about lo 0.01 and 30 grams per litre of culture medium.

Differently from the other commercial culture media, the culture medium of the invention does not need pH adjustments and in the different embodiments thereof has a pH value suitable to the growth and/or isolation and/or identification of the different species of *Mycoplasma*. Preferably the pH of the herein described culture medium is comprised between 7.5 and 7.7.

The culture medium of the invention can be prepared on laboratory scale by means of any process considered suitable by the person skilled in the art. In an exemplifying and not limiting embodiment, such process can consists in weighing the different main ingredients/components separately and in adding gradually a liquid to the mixture of powders, until obtaining the complete dissolution thereof. The suspension is stirred and left to rest for at least 10 minutes. The culture medium is sterilized at about 115° C. for 10 minutes, and subsequently, after having cooled at 45-50° C. the liquid supplements are added containing the globular and fibrous proteins, the solution of amino acids.

The culture medium can be in liquid, semisolid, solid or even lyophilized form. The culture medium can be then inserted in hermetic phials, protected from light and kept at room temperature.

Generally, the herein described culture medium can be used with different purposes, both in the formulations of culture media for enriching and preserving clinical samples, in the culture media for preserving strains, in the solid culture media for isolating colonies, in including culture media for presumptive identification in test tubes or plates of conventional identification.

In Vitro Method for Isolating Species of Mycoplasmas

Herein also a method for in vitro cultivation and/or isolation and/or identification of microorganisms of *Mycoplasma* genus is described.

In particular, the method characterizes in that it comprises a step of culturing microorganisms by using the culture medium of the invention.

In case of the invention only, samples comprising mycoplasmas will be scattered on a growth support comprising such culture medium and incubated under conditions suitable for growing microorganisms. In particular, these conditions include a cultivation temperature of about 36° C. in the culture medium of the invention in solid or liquid form.

In an embodiment of the invention, the cultivated and/or isolated and/or identified species belong to the species of *Mycoplasma genitalium, Mycoplasma pneumoniae, Mycoplasma penetrans, Mycoplasma fermentans, Mycoplasma pirium* and/or *Mycoplasma hyorhinis*.

In general, the method of the invention makes possible the identification of species of *Mycoplasma* genus in different types of sample, for example, samples with veterinary clinical origin, water samples or environmental general samples as well as in food.

Supports for Isolation and Identification of Species of Mycoplasmas.

The subject of the present description is also a support for the growth and/or isolation and/or identification of microorganisms belonging to the *Mycoplasma* genus comprising a culture medium of the invention.

By way of not limiting example, the support can be a plate made of polypropylene, pvp, polystyrene or PVC, including conical, straight or semi-straight identification wells, with a bottom shaped like U, V, flat or semi-flat, commonly used in microculture techniques or other methods for the immunological and molecular identification, such as PCR or molecular probes, such as the biochemical methods including chromogenic, fluorogenic or colorimetric reactions.

Preferably, the support is in form of a multi-plate well wherein at least one well comprises said culture medium.

In an embodiment of the invention, said plate comprises at least one well, preferably all wells, with a truncated cone shape.

Kit

Herein a kit for the growth and/or isolation and/or identification of microorganisms belonging to the *Mycoplasma* genus is also described, comprising at least an aliquot of the culture medium of the invention and means suitable to allow the growth and/or isolation and/or identification of said microorganisms. For example, such means can comprise one or more multi-well plates, preferably having wells with a truncated cone shape, instructions for executing the method.

EXAMPLES

The following examples are shown by way of illustration and they are not intended to limit the invention as otherwise described in the present description.

Example 1

A series of mixtures of nutritional bases were tested as nutritional components in the formulation. In the experiments, 3 variants were designed, the composition thereof is shown in Table 1. The ingredients were reconstituted in 100 mL of water and prepared according to the detailed description of the present invention.

The evaluation of the capability to promote the growth was implemented with collection strains with respect to the reference culture medium (ATCC® Medium 2611: Spiroplasma medium). In each test tube 0.1 mL of the standardized solution of each microorganism was inoculated.

The results of the promotion of growth of the different species of mycoplasmas were highly satisfying. In case of *Mycoplasma pneumoniae*, it was observed that the 3 compositions characterizing the present invention promoted with greater intensity the growth, during the first 49-72 hours, with respect to the control medium which was more than 7 days.

In case of *Mycoplasma penetrans* a greater growth acceleration was observed in the first three days, in the experimental variants, with reference to the check, and in case of *Mycoplasma genitalium* starting from 3-5 days.

TABLE 1

Composition of nutritional bases of the different experimental variants (VS).

| Composition | $VS_1$ (g/L) | $VS_2$ (g/L) | $VS_3$ (g/L) |
|---|---|---|---|
| *S.cerevisiae* autolysate | 15 | 30 | 45 |
| Extract from beef heart | 1 | 10 | 20 |
| Hydrolysate of bovine blood | 5 | 29 | 10 |
| Enzymatic hydrolysate of milk proteins | 5 | 34 | 10 |
| Enzymatic hydrolysed of soybeans proteins | 1 | 2.5 | 4.9 |
| Enzymatic hydrolysed of animal tissue | 1 | 25 | 43.5 |
| Glucose | 1 | 10 | 20 |

Example 2

The composition was prepared with the ingredients, according to example 1, but weighed separately inside an Erlenmeyer flask. As growth-promoting agents and enzymatic markers, the following ingredients were used:

150 mL of inactivated horse serum

Cytidine monophosphate: 0.002-5 gr

Mixture of amino acids 1%

L-Cystine.2HCl 0.06 gr

Mixture of water-soluble and lipo-soluble vitamins 1%

HEPES 2 gr

Mixture of antimicrobial agents: 0.5 g/L vancomycin, 0.2 g/L nystatin, 0.03 g/L phenol red, 0.1 g/L penicillin pH=7.5 (+0.2)

The following collection strains were inoculated:

| | |
|---|---|
| *Mycoplasma hominis* | ATCC 23114 |
| *Mycoplasma penetrans* | ATCC 55252 |
| *Ureaplasma urealyticum* | ATCC 27618 |
| *Ureaplasma urealyticum* | ATCC 33175 |
| *Ureaplasma parvum* | ATCC 27815 |
| *Mycoplasma genitalium* | ATCC 33175 |
| *Mycoplasma fermentans* | ATCC 19989 |
| *Mycoplasma hyorhinis* | ATCC 29052 |
| *Mycoplasma pirum* | ATCC 25960 |

Such strains were inoculated directly, in test tube, with a solution standardized at 10 UCC.

The grey squares mean that starting from that moment the cultures are not read anymore as they have already reached positive values and it is not necessary to continue the experiment.

| | READING | | | | |
|---|---|---|---|---|---|
| STRAINS | 24 H | 48 H | 72 H | 4 G | 6 G |
| *Mycoplasma hominis* ATCC 23114 | − | + | | | |
| *Mycoplasma penetrans* ATCC 55252 | − | − | − | − | − |
| *Mycoplasma pirum* ATCC 25960 | − | − | − | − | − |
| *Mycoplasma hyorhinis* ATCC 29052 | − | − | − | − | − |
| *Mycoplasma fermentans* ATCC 19989 | − | − | − | − | − |
| *Mycoplasma genitalium* ATCC 33175 | − | − | − | − | − |
| *Ureaplasma parvum* ATCC 27815 | − | + | | | |
| *Ureaplasma urealyticum* ATCC 33175 | + | | | | |
| *Ureaplasma urealyticum* ATCC 27618 | + | | | | |

Example 3

The composition of the culture medium was prepared according to example 2, with the difference that the concentration of the nutritional components and of the enzymatic markers (VS2) was increased. Separately, inside an Erlenmeyer flask the following amounts were weighed:

150 mL of inactivated horse serum 10 mL of bovine fetal serum

Components from soyabean extracts (25%), cholesterol (2%), albumin (5%).

Mixture of amino acids: 5%

L-Cystine.2HCl:1 gr

Mixture of water-soluble and lipo-soluble vitamins 17%

HEPES 2 gr

Mixture of antimicrobial agents: 0.1-3.4 g/L nalidixic acid, 0.5-1 g/L vancomycin, 0.2-5 g/L nystatin, 0.05 g/L phenol red, 0.1 g/L penicillin, 0.05 g/L amphotericin B.

| STRAINS | READING | | | | |
|---|---|---|---|---|---|
| | 24 H | 48 H | 72 H | 4 G | 6 G |
| *Mycoplasma hominis* ATCC 23114 | – | + | | | |
| *Mycoplasma penetrans* ATCC 55252 | – | – | – | – | – |
| *Mycoplasma pirum* ATCC 25960 | – | – | – | – | – |
| *Mycoplasma hyorhinis* ATCC 29052 | – | – | – | – | – |
| *Mycoplasma fermentans* ATCC 19989 | – | – | – | – | – |
| *Mycoplasma genitalium* ATCC 33175 | – | – | – | – | – |
| *Ureaplasma parvum* ATCC 27815 | – | + | | | |
| *Ureaplasma urealyticum* ATCC 33175 | – | + | | | |
| *Ureaplasma urealyticum* ATCC 27618 | – | + | | | |

Example 4

The composition of the culture medium was prepared according to example 2, with the difference that the concentration of the nutritional components and of the enzymatic markers (VS3) was increased. Separately, inside an Erlenmeyer flask the following amounts were weighed:

100 mL of inactivated horse serum 50 mL of inactivated swine serum 50 mL of bovine fetal serum Globular proteins: 0.7 gr Fibrous proteins: 1 gr Growth factors in suspension constituted by denaturated plasmatic proteins (2%), lipids (8%), amino acids/aminonucleotides (4%), cholesterol (2%), albumin (0.1%).

Cytidine monophosphate: 0.005 gr

Mixture of amino acids 3%

L-Cystine.2HCl 0.1 gr

Mixture of water-soluble and lipo-soluble vitamins 3%

HEPES 0.05 gr

Mixture of antimicrobial agents: 0.1-3.4 g/L nalidixic acid, 0.5-1 g/L vancomycin, 0.2-5 g/L nystatin, 0.01-0.5 g/L thallium acetate, 0.03-3 g/L phenol red, 0.1-5 g/L penicillin, 0.05-3 g/L amphotericin B, 0.55 a 1.6 g/L thallium acetate.

pH=7.5 (+0.2)

| STRAINS | READING | | | | |
|---|---|---|---|---|---|
| | 24 H | 48 H | 72 H | 4 G | 6 G |
| *Mycoplasma hominis* ATCC 23114 | – | + | | | |
| *Mycoplasma penetrans* ATCC 55252 | – | – | – | + | |
| *Mycoplasma pirum* ATCC 25960 | – | – | – | – | – |
| *Mycoplasma hyorhinis* ATCC 29052 | – | – | – | – | – |
| *Mycoplasma fermentans* ATCC 19989 | – | – | + | | |
| *Mycoplasma genitalium* ATCC 33175 | – | – | – | – | – |
| *Ureaplasma parvum* ATCC 27815 | – | + | | | |
| *Ureaplasma urealyticum* ATCC 33175 | – | + | | | |
| *Ureaplasma urealyticum* ATCC 27618 | – | + | | | |

Example 5

The composition of the culture medium was prepared by weighing the ingredients separately inside an Erlenmeyer flask (VS3). Two mixtures of inhibitors in the solid culture medium were experimented. Hereinafter the composition of used growth-promoting agents, enzymatic markers and inhibitors is described:

To be added aseptically:

100 mL of inactivated horse serum 100 mL of inactivated swine serum 100 mL of bovine fetal serum Globular proteins: 70 gr Fibrous proteins: 30 gr Growth factors in suspension constituted by denaturated plasmatic proteins (15%), lipids (10%), amino acids/aminonucleotides (22%), cholesterol (10%), albumin (5%).

Cytidine monophosphate: 0.1 gr

Mixture of amino acids 30%

L-Cystine.2HCl 0.5 gr

Mixture of water-soluble and lipo-soluble vitamins 15%

HEPES 0.02 gr

Mixture of antimicrobial agents: 0.4 g/L nalidixic acid, 0.5 g/L vancomycin, 0.5 g/L nystatin, 0.05 g/L thallium acetate, 0.03 g/L phenol red, 0.5 g/L penicillin, 0.03 g/L amphotericin B pH=7.5 (+0.2)

| STRAINS | READING | | | | |
|---|---|---|---|---|---|
| | 24 H | 48 H | 72 H | 4 G | 6 G |
| *Mycoplasma hominis* ATCC 23114 | + | | | | |
| *Mycoplasma penetrans* ATCC 55252 | – | + | – | + | |
| *Mycoplasma pirum* ATCC 25960 | – | – | – | – | + |
| *Mycoplasma hyorhinis* ATCC 29052 | – | – | – | – | + |
| *Mycoplasma fermentans* ATCC 19989 | – | + | | | |
| *Mycoplasma genitalium* ATCC 33175 | – | – | – | – | + |
| *Ureaplasma parvum* ATCC 27815 | – | + | | | |
| *Ureaplasma urealyticum* ATCC 33175 | – | + | | | |
| *Ureaplasma urealyticum* ATCC 27618 | – | + | | | |

In the evaluation the following strains were used: *Proteus mirabilis* ATCC 7002, *Proteus mirabilis* ATCC 12433, *Staphylococcus epidermidis* ATCC 12228, *Staphylococcus aureus* ATCC 25923, *Staphylococcus xylosus* ATCC 29971, *Staphylococcus saprophyticus* ATCC 43867, *Enterococcus faecium* ATCC 6056, *Streptococcus agalactiae* ATCC 12386, *Streptococcus faecalis* ATCC 29212.

None of this species grew in the described formulation.

Example 6

The composition of the culture medium was prepared by weighing the ingredients separately inside an Erlenmeyer flask. The culture medium was prepared with the same relation of nutritional bases of example 5, with the exception of the fact that enzymatic hydrolysate of animal tissue was added, in the following amount: 45 g/500 mL. Furthermore two different enzymatic markers were tested, in concentration equal to 1.0 g/L, with addition of 0.5 g/L of ferric ammonium citrate and nalidixic acid in two different concentrations: 0.015 g/L and 0.010 g/L.

To be added aseptically:

100 mL of inactivated horse serum 100 mL of inactivated swine serum 100 mL of bovine fetal serum Globular proteins: 50 gr Fibrous proteins: 50 gr Growth factors in suspension constituted by denaturated plasmatic proteins (20%), lipids (10%), amino acids/aminonucleotides (30%), components from soyabean extracts (2%), cholesterol (30%), albumin (0.5%).

Cytidine monophosphate: 0.02 gr

Mixture of amino acids 45%

L-Cystine.2HCl 0.1 gr

Mixture of water-soluble and lipo-soluble vitamins 20%

HEPES 0.5 gr

Mixture of antimicrobial agents: 0.4 g/L nalidixic acid, 1 g/L vancomycin, 0.5 g/L nystatin, 0.05 g/L thallium acetate, 0.05 g/L phenol red, 0.5 g/L penicillin, 0.2 g/L amphotericin B.

pH=7.5 (+0.2)

| | READING | | | | |
|---|---|---|---|---|---|
| STRAINS | 24 H | 48 H | 72 H | 4 G | 6 G |
| *Mycoplasma hominis* ATCC 23114 | + | | | | |
| *Mycoplasma penetrans* ATCC 55252 | − | + | − | | |
| *Mycoplasma pirum* ATCC 25960 | − | − | − | + | |
| *Mycoplasma hyorhinis* ATCC 29052 | − | − | +/− | + | |
| *Mycoplasma fermentans* ATCC 19989 | − | + | | | |
| *Mycoplasma genitalium* ATCC 33175 | − | − | +/− | + | |
| *Ureaplasma parvum* ATCC 27815 | − | + | | | |
| *Ureaplasma urealyticum* ATCC 33175 | − | + | | | |
| *Ureaplasma urealyticum* ATCC 27618 | − | + | | | |

In the evaluation the following strains were used: *Proteus mirabilis* ATCC 7002, *Proteus mirabilis* ATCC 12433, *Staphylococcus epidermidis* ATCC 12228, *Staphylococcus aureus* ATCC 25923, *Staphylococcus xylosus* ATCC 29971, *Staphylococcus saprophyticus* ATCC 43867, *Enterococcus faecium* ATCC 6056, *Streptococcus agalactiae* ATCC 12386, *Streptococcus faecalis* ATCC 29212.

None of this species grew in the described formulation.

The invention has been so far described with reference to the embodiments. As it will result evident to the person skilled in the art from what detailed, additional embodiments belonging to the same inventive core could be also provided which, then, will have to meant as included within the protective scope defined by the claims of the present application.

BIBLIOGRAPHY

1. BARILE, M. F., R. YAGUCHI, AND W. C. EVELAND. 1958. A simplified medium for the cultivation of pleuropneumonia-like organisms and L-forms of bacteria. Am. J. Clin. Pathol. 30:171-176.
2. HAYFLICK, L., AND R. M. CHANOCK. 1965. *Mycoplasma* species of man. Bacteriol. Rev. 29:185-221.
3. BARILE, M. F., W. F. MALIZIA, AND D. B. RIGGS. 1962. Incidence and detection of pleuropneumonia-like organisms in cell cultures by fluorescent antibody and cultural procedures. J. Bacteriol. 84:130-136.
4. BARILE, M. F., AND R. T. SCHIMKE. 1963. A rapid chemical method of detecting PPLO contamination of tissue cell culture. Proc. Soc. Exptl. Biol. Med. 114:676-679.
5. CHALQUEST, R. R., AND J. FABRICANT. 1960. Pleuropneumonia-like organisms associated with synovitis in fowl. Avian Diseases 4:515-539.
6. CHANOCK, R. M., L. HAYFLICK, AND M. F. BARILE. 1962. Growth on artificial medium of an agent associated with atypical pneumonia and its identification as a PPLO. Proc. Natl. Acad. Sci. U.S. 48:41-49.
7. EDWARD, D. G. FF., AND E. A. FREUNDT. 1956. The classification and nomenclature of organisms of the pleuropneumonia group. J. Gen. Microbiol. 14:197-207.
8. FABRICANT, J. 1960. Serological studies of avian pleuropneumonia-like organisms (PPLO) with Edward's technique. Avian Diseases 4:505-514.
9. HAYFLICK, L., AND R. M. CHANOCK. 1965. *Mycoplasma* species of man. Bacteriol. Rev. 29:185-221.
10. GOURLAY R. N., WYLD S. G. & LEACH R. H. (1977) *Mycoplasma alvi*, a new species from bovine intestinal and urogenital tracts. Int. J. Syst. Bacteriol. 27, 86-96.

11. GOURLAY R. N., WYLD S. G. & LEACH R. H. (1978) *Mycoplasma sualvi*, a new species from the intestinal and urogenital tracts of pigs. Int. J. Syst. Bacteriol. 28, 289-292.
12. HORNER et al. (1993) Association of *Mycoplasma genitalium* with acute non-gonococcal urethritis. Lancet 342, 582-585.
13. Hu P. C., SCHAPER U., COLLIER A. M., CLYDE W. A. J., HORIKAWA M., HUANG Y. S. & BARILE M. F. (1987) A *Mycoplasma genitalium* protein resembling the *Mycoplasma pneumoniae* attachment protein. Infect. Immun. 55, 1126-1131.
14. JENSEN J. S., ORSUM R., DOHN B., ULDUM S., WORM A.-M. & LIND K. (1993) *Mycoplasma genitalium*: a cause of male urethritis? Genitourin. Med. 69, 265-269.
15. JENSEN J. S., ULDUM S. A., SONDERGARD-ANDERSEN J., VUUST J. & LIND K. (1991) Polymerase chain reaction for detection of *Mycoplasma genitalium* in clinical samples. J. Clin. Microbiol. 29, 46-50.
16. TAYLOR-ROBINSON D., DAVIES H. A., SARATHCHANDRA P. & FURR P. M. (1991) Intracellular location of mycoplasmas in cultured cells demonstrated by immunocytochemistry and electron microscopy. Int. J. Exp. Pathol. 72, 705-714.
17. LIND K. & KRISTENSEN G. B. (1987) Significance of antibodies to *Mycoplasma genitalium* in salpingitis. Eur. J. Clin. Microbiol. 6, 205-207.
18. LIND K., LINDHARDT B. O., SCHOUTEN H. J., BLOM J. & CHRISTIANSEN C. (1984) Serological cross-reactions between *Mycoplasma genitalium* and *Mycoplasma pneumoniae*. J. Clin. Microbiol. 20, 1036-1043.
19. Lo S. C., DAWSON M. S., WONG D. M., NEWTON P. B., SONODA M. A., ENGLER W. F., WANG R. Y., SHIH J. W., ALTER H. J. & WEAR D. J. (1989) Identification of *Mycoplasma incognitus* infection in patients with AIDS: an immunohistochemical, in situ hybridization and ultrastructural study. Am. J. Trop. Med. Hyg. 41, 601-616.
20. Lo S. C., HAYES M. M., TULLY J. G., WANG R. Y., KOTANI H., PIERCE P. F., ROSE D. L. & SHIH J. W. (1992) *Mycoplasma penetrans* sp. nov., from the urogenital tract of patients with AIDS. Int. J. Syst. Bacteriol. 42, 357-364.
21. PALMER H. M., GILROY C. B., CLAYDON E. J. & TAYLOR-ROBINSON D. (1991) Detection of *Mycoplasma genitalium* in the genitourinary tract of women by the polymerase chain reaction. Int. J. STD. AIDS 2, 261-263.
22. TAYLOR-ROBINSON D., DAVIES H. A., SARATHCHANDRA P. & FURR P. M. (1991) Intracellular location of mycoplasmas in cultured cells demonstrated by immunocytochemistry and electron microscopy. Int. J. Exp. Pathol. 72, 705-714.
23. TAYLOR-ROBINSON D., FURR P. M. & HANNA N. F. (1985) Microbiological and serological study of non-gonococcal urethritis with special reference to *Mycoplasma genitalium*. Genitourin. Med. 61, 319-324.
24. TULLY J. G., TAYLOR-ROBINSON D., COLE R. M. & ROSE D. L. (1981) A newly discovered *mycoplasma* in the human urogenital tract. Lancet I, 1288-1291.
25. TULLY J. G., TAYLOR-ROBINSON D., ROSE D. L., COLE R. M. & BOVE J. M. (1983) *Mycoplasma genitalium*, a new species from the human urogenital tract. Int. J. Syst. Bacteriol. 33, 387-396.

26. Clyde, W. A. (1964). *Mycoplasma* species identification based upon growth inhibition by specific antisera. Journal of Immunology 92, 958-65.

27. Ainsworth, J. G., Katseni, V., Hourshid, S., Waldron, S., Ba Cattell, V. et al. (1994). *Mycoplasma fermentans* and HIV associated nephropathy. Journal of Infection 29, 323-6.

28. Hawkins, R. E., Rickman, L. S., Vermund, S. H. & Carl, M. (1992). Association of *mycoplasma* and human immunodeficiency virus infection: detection of amplified *Mycoplasma fermentans* DNA in blood. Journal of Infectious Diseases 165, 581-5.

29. Katseni, V. L., Gilroy, C. B., Ryait, B. K., Ariyoshi, K., Bieniasz, P. D., Weber, J. N. et al. (1993). *Mycoplasma fermentans* in individuals seropositive and seronegative for HIV-1. Lancet 341, 271-3.

30. Lo, S.-C., Wear, D. J., Green, S. L., Jones, P. G. & Legier, J. F. (1993). Adult respiratory distress syndrome with or without systemic disease associated with infections due to *Mycoplasma fermentans*. Clinical Infectious Diseases 17, Suppl. 1, S259-63.

31. Damassa y cols, 1992. *Mycoplasma* of goats and sheep. J. Vet Diagn Invest. 1992 January; 4(1): 101-13

The invention claimed is:

1. A method for in vitro cultivating, isolating, and/or identifying *Mycoplasma* and/or *Ureaplasma* genus microorganisms comprising culturing the microorganisms of *Mycoplasma* and/or *Ureaplasma* genus in a culture medium comprising:
- hydrolysate of bovine blood;
- extract from beef heart;
- enzymatic hydrolysate of bovine heart;
- enzymatic hydrolysate of milk proteins;
- enzymatic hydrolysate of soybeans proteins;
- enzymatic hydrolysate of animal tissue;
- autolysate or hydrolysate from *Sacharomyces cerevisiae;*
- salts of trivalent metals;
- aromatic amino acids;
- a mixture of globular protein and plasma; and
- fibrous proteins, and isolating the microorganisms of *Mycoplasma* and/or *Ureaplasma* genus by evaluating a color change in the medium;

wherein red or turbid red indicates *Mycoplasma hominis;* red indicates *Ureaplasma urealyticum* or *Ureaplasma parvum;* turbid yellow indicates *Mycoplasma* pneumonia or *Mycoplasma hyorhinis;* orange or yellow indicates *Mycoplasma genitalium;* brilliant yellow or turbid yellow indicates *Mycoplasma fermentans* or *Mycoplasma penetrans*; and yellow or turbid yellow indicates *Mycoplasma pirum.*

2. The method according to claim 1, wherein the microorganisms of *Mycoplasma* and/or *Ureaplasma* genus include *Mycoplasma genitalium, Mycoplasma pneumoniae, Mycoplasma penetrans, Mycoplasma fermentans, Mycoplasma pirium Mycoplasma hyorhinis, Mycoplasma hominis, Ureaplasma urealyticum* and/or *Ureaplasma parvum.*

3. The method according to claim 1, wherein the culture media further comprises growth inhibitors of Gram-negative microorganisms, Gram-positive microorganisms, fungi, and yeasts.

4. The method according to claim 3, wherein said inhibitors are selected from nalidixic acid, vancomycin, nystatin, thallium acetate, phenol red, penicillin, or amphotericin B.

5. The method according to claim 4, wherein the nalidixic acid is present in an amount comprised between 0.1 and 3.5 grams per litre of culture medium; and/or the vancomycin is present in an amount comprised between 0.5 and 1 gram per litre of culture medium; and/or the nystatin is present in an amount comprised between 0.2 and 5 grams per litre of culture medium; and/or the thallium acetate is present in an amount comprised between 0.01 and 1.5 grams per litre of culture medium; and/or the phenol red is present in an amount comprised between 0.03 and 3 grams per litre of culture medium; and/or the penicillin is present in an amount comprised between 0.1 and 5 grams per litre of culture medium; and/or the amphotericin B is present in an amount comprised between 0.05 and 3 grams per litre of culture medium.

6. The method according to claim 1, wherein the extract from beef heart is present in an amount between about 2 and 56 grams per litre of culture medium; and/or the hydrolysate of bovine blood is present in an amount between about 5 and 30 grams per litre of culture medium; and/or the enzymatic hydrolysate of bovine heart is present in an amount between about 1 and 62 grams per litre of culture medium; and/or the enzymatic hydrolysate of milk proteins is present in an amount between about 1 and 67 grams per litre of culture medium; and/or the enzymatic hydrolysate of soybean proteins is present in an amount between about 0.2 and 34 grams per litre of culture medium; and/or the enzymatic hydrolysate of animal tissue is present in an amount between about 2 and 99 grams per litre of culture medium; and/or the autolysate or hydrolysate from *Saccharomyces cerevisiae* is present in an amount between about 15 and 56 grams per litre of culture medium.

7. The method according to claim 1, wherein the salts of trivalent metals are present in an amount comprised between about 0.5 and 1.0 grams per litre of culture medium; and/or the aromatic amino acids are present in an amount comprised between about 1 and 72 grams per litre of culture medium; and/or the mixture of globular proteins and plasma is present in an amount comprised between about 0.01 and 70 grams per litre of culture medium.

8. The method according to claim 1, wherein the culture media has a pH value between 7.5 and 7.7.

9. The method according to claim 1, wherein the culture media is in at least a form of a liquid, a semi-solid, solid, or lyophilized form.

* * * * *